United States Patent
Birrer et al.

(10) Patent No.: US 8,975,438 B2
(45) Date of Patent: Mar. 10, 2015

(54) PROCESS FOR THE PREPARATION OF CYCLOHEXANECARBOXYLIC ACID DERIVATIVES

(75) Inventors: Beat Birrer, Kaiseraugst (CH); Leo Clarke, County Clare (IL); Walter Deichtmann, Village-Neuf (FR); John Hayes, County Clare (IL); Julius Jeisy, Pfeffingen (CH); Christian Lautz, Denzlingen (DE); Rainer E. Martin, Basel (CH); Michael Meade, County Clare (IL); Joaquim Pintao, County Clare (IL); Michelangelo Scalone, Birsfelden (CH); Juergen Schaefer, Rheinfelden (DE); Dennis Smith, County Clare (IL); Andreas Staempfli, Binningen (CH); Joachim Veits, Florence, SC (US); Christian Walch, Rixheim (FR); Andrew Walsh, County Clare (IL); Andreas Zogg, Frenkendorf (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/541,795

(22) Filed: Jul. 5, 2012

(65) Prior Publication Data

US 2013/0018201 A1 Jan. 17, 2013

(30) Foreign Application Priority Data

Jul. 13, 2011 (EP) ..................................... 11173736

(51) Int. Cl.
| | |
|---|---|
| C07C 259/04 | (2006.01) |
| C07C 319/20 | (2006.01) |
| C07C 51/06 | (2006.01) |
| C07C 51/08 | (2006.01) |
| C07C 319/06 | (2006.01) |
| C07C 327/30 | (2006.01) |
| C07C 51/02 | (2006.01) |

(52) U.S. Cl.
CPC ............... *C07C 319/20* (2013.01); *C07C 51/06* (2013.01); *C07C 51/08* (2013.01); *C07C 319/06* (2013.01); *C07C 327/30* (2013.01); *C07C 51/02* (2013.01); *C07C 2101/14* (2013.01)
USPC .......................................................... 562/622

(58) Field of Classification Search
None
See application file for complete search history.

(56) References Cited

U.S. PATENT DOCUMENTS

2009/0253927 A1* 10/2009 Hoffmann et al. ............ 558/257
2009/0253928 A1* 10/2009 Harnett et al. ................ 558/257

FOREIGN PATENT DOCUMENTS

| EP | 0077551 | 4/1983 |
|---|---|---|
| WO | 2007/051714 | 5/2007 |
| WO | 2009/121788 | 10/2009 |
| WO | 2009/121789 | 10/2009 |
| WO | 2009/153181 | 12/2009 |
| WO | 2011/000793 | 1/2011 |

OTHER PUBLICATIONS

Advanced Organic Chemistry : Reactions, Mechanisms, and Structure , Mar. 1992, pp. 887-888.*
Kobayashi et al., Atherosclerosis 162:131-135 ( 2002).
Shinkai et al., J. Med. Chem. 43:3566-3572 ( 2000).
De Grooth et al., Circulation 105:2159-2165 ( 2002).
Okamoto et al., Nature 406(13):203-207 ( 2000).
Goss et al., Organic & Biomolecular Chemistry (XP55012393), 4(22):4071-4073 (2006).
March, J. Advanced Organic Chemistry (XP002663765), 3rd edition, John Wiley & Sons,:788 (1985).
(International Search Report for PCT/EP2012/063455 Nov. 5, 2012).
Theobold, Tetrahedron (XP55012396), 21(4):791-796 ( 1965).
Shao et al., Bioorganic & Medicinal Chemistry Letters (XP55012388), 21(5):1438-1441 (2011).

* cited by examiner

*Primary Examiner* — Karl J Puttlitz

(57) ABSTRACT

A process for the preparation of a compound of formula (I):

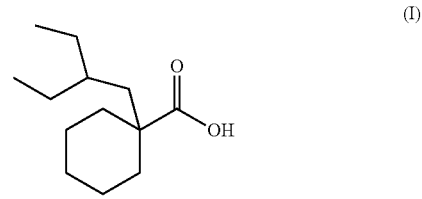

which is useful as an intermediate in the preparation of pharmaceutically active compounds.

10 Claims, No Drawings

PROCESS FOR THE PREPARATION OF CYCLOHEXANECARBOXYLIC ACID DERIVATIVES

PRIORITY TO RELATED APPLICATION(S)

This application claims the benefit of European Patent Application No. 11173736.7, filed Jul. 13, 2011, which is hereby incorporated by reference in its entirety.

BACKGROUND OF THE INVENTION

S-[2-([[1-(2-ethylbutyl)cyclohexyl]carbonyl]amino)phenyl]2-methylpropanethioate has been shown to be an inhibitor of CETP activity in humans (de Grooth et al., Circulation, 105, 2159-2165 (2002)) and rabbits (Shinkai et al., J. Med. Chem., 43, 3566-3572 (2000); Kobayashi et al., Atherosclerosis, 162, 131-135 (2002); and Okamoto et al., Nature, 406 (13), 203-207 (2000). Thus, alternative methods of synthesizing certain intermediates such as 1-(2-ethyl-butyl)-cyclohexanecarboxylic acid used in the manufacture of S-[2-([[1-(2-ethylbutyl)cyclohexyl]carbonyl]amino)phenyl]2-methylpropanethioate remains important.

SUMMARY OF THE INVENTION

The present invention relates to a process for the preparation of a cyclohexanecarboxylic acid derivative which is useful as an intermediate in the preparation of pharmaceutically active compounds.

DETAILED DESCRIPTION OF THE INVENTION

Unless otherwise stated, the following terms used in the specification and claims have the meanings given below:

The term "halo" means fluoro, chloro, bromo or iodo. In particular embodiments halo is chloro or bromo.

The term "$(C_1\text{-}C_8)$alkyl" refers to a branched or straight hydrocarbon chain having 1-8 carbon atoms. Examples include methyl, ethyl, n-propyl, isopropyl, n-butyl, isobutyl, sec-butyl, t-butyl, pentyl, hexyl, heptyl and octyl. Similarly, the term "$(C_1\text{-}C_3)$alkyl" refers to a branched or straight hydrocarbon chain having 1-3 carbon atoms. Examples include methyl, ethyl, n-propyl and isopropyl.

The term "alkali metal" or "alkali" refers to lithium, sodium, potassium, rubidium, or cesium. In particular embodiments the alkali metal is potassium or sodium. In more particular embodiments the alkali metal is sodium.

The term "base" refers to an aqueous base or an inorganic base.

The term "inorganic base" refers to an alkali metal base, such as alkali carbonate, alkali bicarbonate, alkali borate, alkali phosphate or alkali-hydroxide. In particular embodiments, the inorganic base is an alkali hydroxide. More particularly the inorganic base is KOH or NaOH. More particularly the inorganic base is NaOH. In particular embodiments, the inorganic base is solid and more particularly solid pellets.

The term "aqueous base" refers to a solution comprising a base and water. Numerous bases which readily dissolve in water are known in the art, such as alkali carbonate, alkali bicarbonate, alkali borate, alkali phosphate and alkali-hydroxide. In particular embodiments, the aqueous base is a solution comprising water and NaOH, KOH, LiOH, $Ca(OH)_2$ or $Mg(OH)_2$, and more particularly is a solution comprising water and NaOH or KOH. In more particular embodiments, the aqueous base refers to solution comprising water and NaOH.

The term "alcohol" refers to benzyl alcohol, aminoethanol or a $(C_{1\text{-}8})$alkyl substituted by one or two hydroxy groups. In particular embodiments, the alcohol is a $(C_1\text{-}C_3)$alkyl substituted by one or two hydroxy groups. In particular embodiments the alcohol is a $(C_{1\text{-}8})$alkyl or a $(C_1\text{-}C_3)$alkyl substituted by one hydroxy group. Examples of alcohols include, but are not limited to, methanol, ethanol, isopropanol, propanol, propyleneglycol, butanol, t-butanol, benzyl alcohol, 2-aminoethanol and octanol. In particular embodiments, the alcohol is methanol, ethanol or benzylalcohol, and more particularly methanol or ethanol, and most particularly methanol.

The term "equivalent" refers to molar equivalent.

In a first embodiment, the present invention provides a process for the preparation of a compound of formula (I):

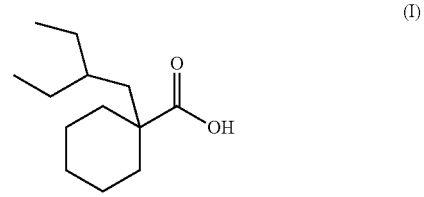

comprising reacting a compound of formula (II):

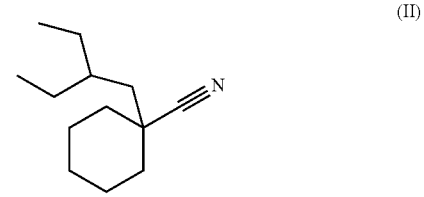

with a base optionally in the presence of water.

The compound of formula (I) may be used as an intermediate in the synthesis of valuable pharmaceutical compounds. For example, 1-(2-ethyl-butyl)-cyclohexanecarboxylic acid may be used in the synthesis of the compounds described in European Patent No. 1,020,439.

In a second embodiment, the present invention provides a process for the preparation of a compound of formula (I):

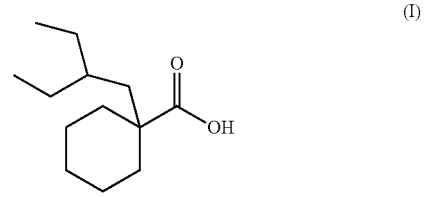

comprising reacting a compound of formula (II):

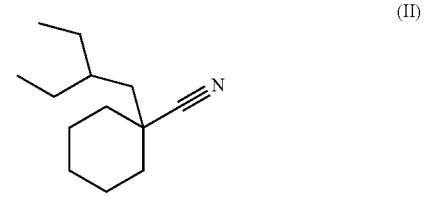

with an aqueous base or with an inorganic base optionally in the presence of water.

In another embodiment, the present invention provides a process for the preparation of a compound of formula (I):

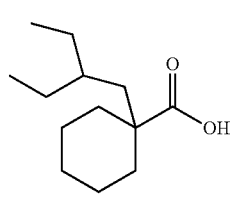
(I)

comprising reacting a compound of formula (II):

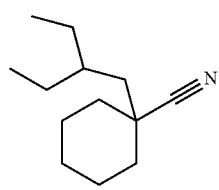
(II)

with an aqueous base.

In another embodiment, the present invention provides a process for the preparation of a compound of formula (I):

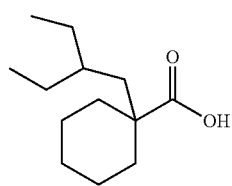
(I)

comprising reacting a compound of formula (II):

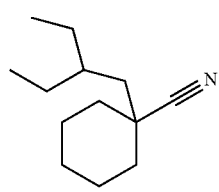
(II)

with an inorganic base optionally in the presence of water.

The present invention provides a one step process for the preparation of a compound of formula (I) comprising reacting a compound of formula (II) with a base optionally in the presence of water.

In another embodiment, the present invention provides a process for the preparation of a compound of formula (I):

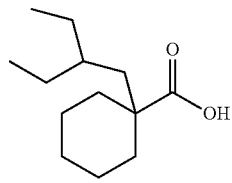
(I)

comprising reacting a compound of formula (II):

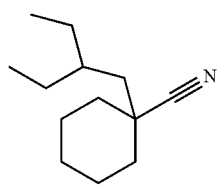
(II)

with an aqueous base or an inorganic base optionally in the presence of water, to obtain a compound of formula (I) via a compound of formula (III):

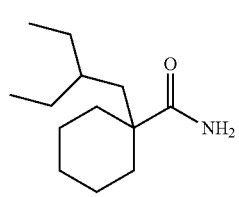
(III)

which is further hydrolysed to a compound of formula (IV):

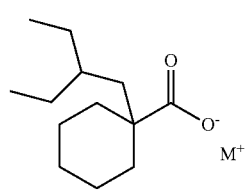
(IV)

wherein $M^+$ is an alkali metal counter ion, to obtain the compound of formula (I).

In another embodiment, the present invention provides a process for the preparation of a compound of formula (I):

(I)

comprising reacting a compound of formula (II):

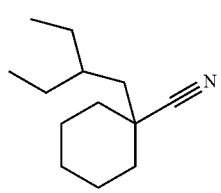
(II)

with aqueous KOH or NaOH; or with KOH or NaOH optionally in the presence of water, to obtain a compound of formula (I) via a compound of formula (III):

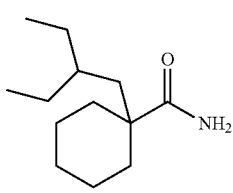

(III)

which is further hydrolysed to a compound of formula (IV):

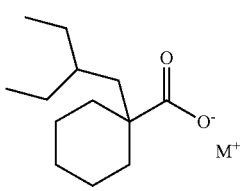

(IV)

wherein M⁺ is a K⁺ or Na⁺ counter ion, to obtain the compound of formula (I).

In another embodiment, the present invention provides a process for the preparation of a compound of formula (I):

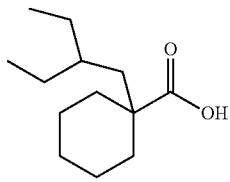

(I)

comprising reacting a compound of formula (II):

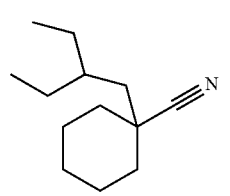

(II)

with aqueous NaOH; or with NaOH, in particular NaOH pellets, optionally in the presence of water, to obtain a compound of formula (I) via a compound of formula (III):

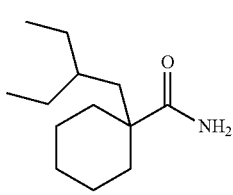

(III)

which is further hydrolysed to a compound of formula (IV):

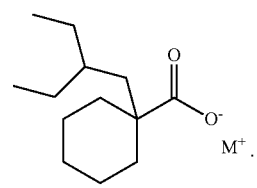

(IV)

wherein M⁺ is a Na⁺ counter ion, to obtain the compound of formula (I).

In another embodiment, the present invention provides a process for the preparation of a compound of formula (I):

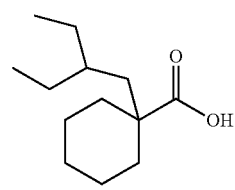

(I)

comprising reacting a compound of formula (II):

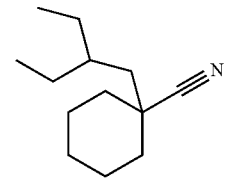

(II)

with aqueous NaOH, to obtain a compound of formula (I) via a compound of formula (III):

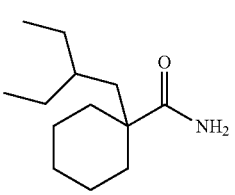

(III)

which is further hydrolysed to a compound of formula (IV):

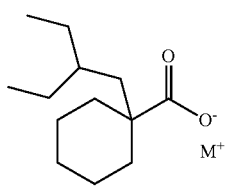

(IV)

wherein M⁺ is a Na⁺ counter ion, to obtain the compound of formula (I).

Accordingly, in another embodiment the present invention provides a process comprising the synthetic steps represented in the following scheme 1:

Scheme 1

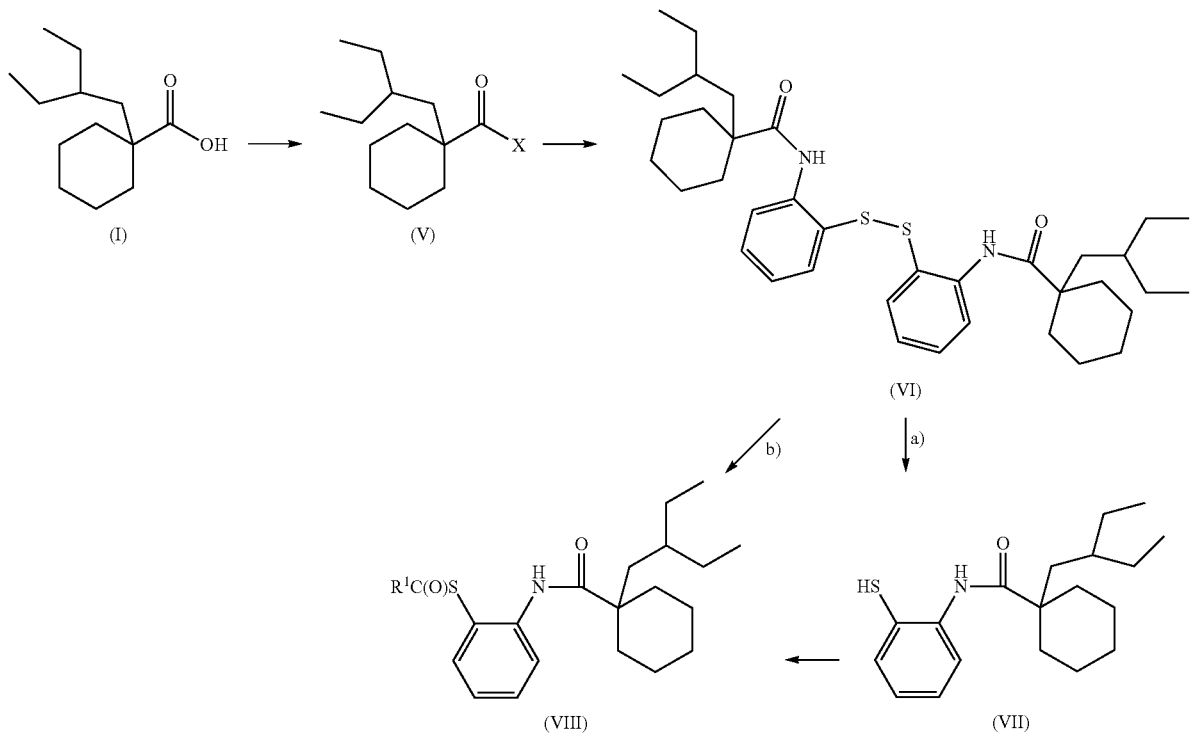

wherein X is I, Br, Cl or F and $R^1$ is a $(C_1\text{-}C_8)$alkyl. In particular, the process comprises reacting a cyclohexanecarboxylic acid derivative of formula (I) with a halogenating agent, such as $PX_3$, $PX_5$, $SOX_2$, NCX or $COX_2$, to obtain the compound of formula (V). The halogenation step is particularly carried out in the presence of a tri-$(C_1\text{-}C_5)$alkylamine. Furthermore, according to route a), the process comprises reacting acyl halide with bis(2-aminophenyl)disulfide to acylate the amino groups of the bis(2-aminophenyl)disulfide, reducing the amino-acylated disulfide product with a reducing agent such as triphenylphosphine, zinc or sodium borohydride to yield the thiol product, and acylating the thiol group in the thiol product with $R^1C(O)X'$, wherein X' is I, Br, Cl or F. Alternatively, via route b), the compound of formula (VI) is reacted with isobutyric anhydride in the presence of a reducing agent, such as a phosphine, phosphinite, phosphonite or phosphite to obtain a compound of formula (VIII) wherein $R^1$ is isopropyl.

The additional steps may be performed, e.g., according to the procedures described in Shinkai et al., J. Med. Chem. 43:3566-3572 (2000), WO 2007/051714, WO2009/153181, WO 2009/121788, WO 2009/121789 or WO 2011/000793.

Particularly, the halogenating agent is chosen from thionyl chloride, phosphorus pentachloride, oxalyl chloride, phosphorus tribromide and cyanuric fluoride, and most particularly thionyl chloride. The compound of formula (V) wherein X is Cl is most preferred.

In the thiol acylation step, the acylating agent is (in particular embodiments) $R^1C(O)X'$, wherein X' is Cl. Most particularly $R^1$ is isopropyl.

In yet another embodiment, the present invention further provides a process for the preparation of a compound of formula (I):

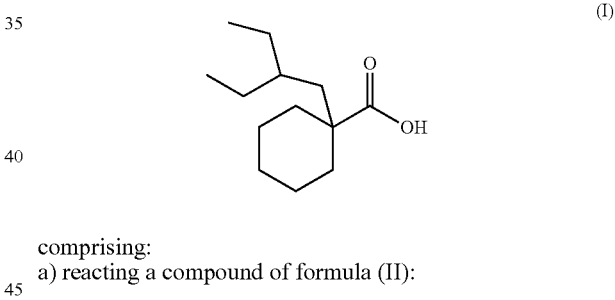

comprising:
a) reacting a compound of formula (II):

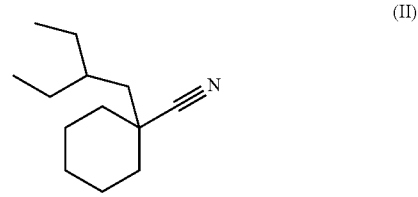

with a base optionally in the presence of water, to obtain a compound of formula (I);
b) followed by addition of a mineral acid, such as hydrofluoric acid, hydrochloric acid, boric acid, nitric acid, phosphoric acid or sulphuric acid, or an organic acid such as formic acid or acetic acid, more particularly the acid is a mineral acid, most particularly hydrochloric acid. In a particular embodiment, the invention provides a process as described herein, wherein the base is an aqueous base or an inorganic base.

In a particular embodiment, the invention provides a process as described herein, wherein the base is an aqueous base.

In a particular embodiment, the invention provides a process as described herein, wherein the base is an inorganic base.

In a particular embodiment, the invention provides a process as described herein, wherein the aqueous base is a solution comprising water and an alkali carbonate, alkali bicarbonate, alkali borate, alkali phosphate or alkali-hydroxide.

In a particular embodiment, the invention provides a process as described herein, wherein the aqueous base is a solution comprising water and NaOH, KOH, LiOH, Ca(OH)$_2$ or Mg(OH)$_2$.

In a particular embodiment, the invention provides a process as described herein, wherein the aqueous base is a solution comprising water and NaOH or KOH.

In a particular embodiment, the invention provides a process as described herein, wherein the aqueous base is a solution comprising water and NaOH.

In a particular embodiment, the invention provides a process as described herein, wherein the inorganic base is an alkali metal base.

In a particular embodiment, the invention provides a process as described herein, wherein the inorganic base is alkali carbonate, alkali bicarbonate, alkali borate, alkali phosphate or alkali-hydroxide.

In a particular embodiment, the invention provides a process as described herein, wherein the inorganic base is an alkali hydroxide.

In a particular embodiment, the invention provides a process as described herein, wherein the inorganic base is KOH or NaOH.

In a particular embodiment, the invention provides a process as described herein, wherein the inorganic base is NaOH.

In a particular embodiment, the invention provides a process as described herein, wherein the inorganic base is solid, and more particularly solid pellets.

In a particular embodiment, the invention provides a process as described herein, wherein the inorganic base is solid NaOH, and more particularly solid NaOH pellets.

In a particular embodiment, the present invention as described herein may be carried out in the presence of an alcohol or a mixture of two or more alcohols. In particular embodiments, the alcohol is methanol, ethanol, tert-butanol or a mixture thereof, and more particularly the alcohol is methanol, ethanol or a mixture thereof, and most particularly the alcohol is methanol.

In particular embodiments, the present invention provides a process as described herein wherein the reaction is carried out at temperature between 150° C. and 280° C., in particular between 150° C. and 250° C., and more particularly between 180° C. to 230° C., and most particularly at 200° C.

In a particular embodiment, the present invention provides a process described herein which uses at least 0.5 equivalents of the aqueous base with respect to a compound of formula (I), and in particular 0.5 to 5.0 equivalents. Particularly 1.0 to 3.0 equivalents are used. More particularly 1.5 to 3.0 equivalents are used. Most particularly 1.5 to 2.5 equivalents are used.

In a particular embodiment, the present invention provides a process described herein which uses at least 0.5 equivalents of the NaOH with respect to a compound of formula (I), and in particular 0.5 to 5.0 equivalents. Particularly 1.0 to 3.0 equivalents are used. More particularly 1.5 to 3.0 equivalents are used. Most particularly 1.5 to 2.5 equivalents are used.

In a particular embodiment, the present invention provides a process described herein which uses at least 0.01 equivalents of the alcohol with respect to compound of formula (I), and in particular 0.01 to 20.0 equivalents. Particularly 5.0 to 12.5 equivalents are used.

In a particular embodiment, the present invention provides a process described herein which uses at least 0.01 equivalents of the alcohol with respect to compound of formula (I), and in particular 0.0 to 20.0 equivalents. Particularly 0.1 to 20.0 equivalents are used. More particularly 5.0 to 12.5 equivalents are used.

In a particular embodiment, the present invention provides a process described herein which uses at least 0.01 equivalents of the water with respect to a compound of formula (I), and in particular 0.0 to 20.0 equivalents of the water with respect to a compound of formula (I). Particularly 0.1 to 20.0 equivalents are used. More particularly 2.0 to 6.0 equivalents are used. In a further embodiment, the present invention provides a process for the preparation of the compound of formula (I), comprising reacting a compound of formula (III) as described above and as described in the following scheme 2, wherein M$^+$ is a defined above.

Scheme 2:

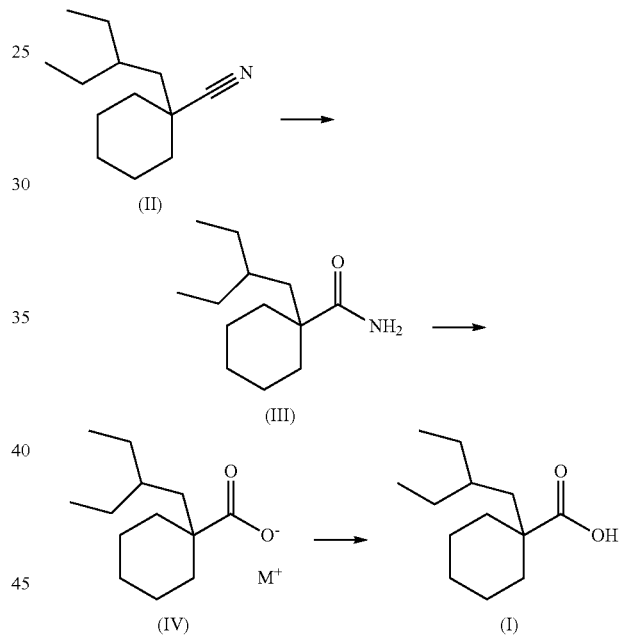

In a further embodiment the present invention provides a process for the preparation of [2-([[1-(2-ethylbutyl)-cyclohexyl]-carbonyl]amino)phenyl]2-methylpropanethioate comprising the formation of a compound of formula (I) obtained by any of the processes and conditions mentioned previously.

In a further embodiment, the present invention provides a compound of formula (IV):

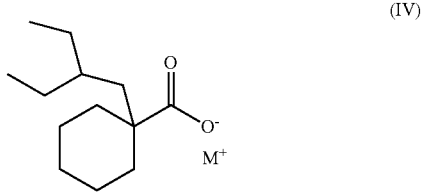

wherein M+ is as defined herein. In particular, the invention provide a compound of formula (IV) wherein M+ is Na+ or K+, and more particularly Na+.

In another embodiment, the present invention provides a process for the preparation of a compound of formula (I) as described above, carried out as semi-continuous or continuous processes, particularly as continuous processes. More particularly, the continuous process is a fluidic flow process. Conducting chemical transformations in microfabricated reactors or tubular coil reactors have been found in many cases advantageous as they lead to better control of chemical process parameters due to extremely high surface to volume ratios. Therefore, these types of reactors provide unique opportunities for chemical engineers to accurately control transport phenomena such as heat and mass transfer (a) C. Wiles, P. Watts, Chem. Commun. 47:6512-6535 (2011); b) *Micro Reaction Technology in Organic Synthesis*, P. Watts, C. Wiles, CRC Press Inc., Boca Raton, 2011; c) *Microreactors in Organic Synthesis and Catalysis*, T. wirth (Ed.), Wiley-VCH, Weinheim, 2008; d) V. Hessel, C. Knobloch, H. Löwe, Recent Pat. Chem. Eng. 1:1-16 (2008)). Unconventional and harsh reaction conditions such as greatly elevated temperatures and pressures can be generated easily, enabling the ability to superheat solvents (organic or aqueous in nature) far beyond their boiling point in a controlled and safe manner opening novel process windows: (a) T. Illg, P. Löb, V. Hessel, Bioorg. Med. Chem. Lett. 18:3707-3719 (2010); (b) V. Hessel, Chem. Eng. Technol. 32:1655-1681 (2009); (c) C. Wiles, P. Watts, Future Med. Chem. 1:1593-1612 (2009); (d) F. Paviou, Pharmaceutical Technology Europe 21:22-32 (2009); and (e) B. P. Mason, K. E. Price, J. L. Steinbacher, A. R. Bogdan, D. T. McQuade, Chem. Rev. 107:2300-2318 (2007)).

Hydrolysis reactions can be conducted as a monophasic (homogeneous) or biphasic (heterogeneous) process. In the case of multiphase reactions fast and efficient mixing of reaction partners represents a unique opportunity for microstructured reactors. In the case of two phase systems there is next to thermal control challenges in addition the complexity of continuously mixing two immiscible liquid solvent streams, which is of particular importance as reaction kinetics are often limited by mass transfer. Rapid mixing often can be achieved by using static mixer elements which maximize the interfacial contact area between the two phases. As the liquid phases move through the mixer, there is continuous blending of the solvent streams by the non-moving passive mixer elements. Numerous novel micromixer designs have emerged over recent years and are described in prior art documents.

When conducting chemical transformations at such high temperatures and pressures with organic and aqueous solvents, the volume expansion is significant and must not be ignored as this would lead to wrong processing times. If the volume expansion of the solvent or solvent mixture is known for a given pressure and temperature, the nominal residence time (quotient from volume of reactor coil and flow rate) can be corrected accordingly providing the so called effective residence time, which describes the actual residence time of the reactant mixture within the heated reactor zone (R. E. Martin, F. Morawitz, C. Kuratli, A. M. Alker, A. I. Alanine, Eur. J. Org. Chem. 47-52 (2012).

The reactor for "discontinuous" or continuous processing, according to the present invention, is made particularly from materials that are oxidation and corrosion resistant materials well suited for operation in extreme environments with respect to temperature and pressure. Such materials form a thick, stable, passivating oxide layer protecting the surface from further attack. Preferred reactor materials are stainless steel or Hastelloy, more preferably austenitic nickel-chromium-based super alloys with a high nickel content such as Monel, Inconel (common trade names: Inconel 600, Inconel 625, Chronin 625) or Chromel (common trade names: Chromel A, Nichrome 80-20); and most preferably pure nickel.

The methods of the present invention may be carried out as semi-continuous or continuous processes, more particularly as continuous processes.

The starting materials and reagents, which do not have their synthetic route explicitly disclosed herein, are generally available from commercial sources or are readily prepared using methods well known to the person skilled in the art. For instance, the compound of formula (II) can be prepared according to the procedures described in WO 2009/121788 or WO 2009/121789.

In general, the nomenclature used in this Application is based on AUTONOM™ 2000, a Beilstein Institute computerized system for the generation of IUPAC systematic nomenclature. Chemical structures shown herein were prepared using MDL ISIS™ version 2.5 SP2. Any open valency appearing on a carbon, oxygen or nitrogen atom in the structures herein indicates the presence of a hydrogen atom.

The following examples are provided for the purpose of further illustration and are not intended to limit the scope of the claimed invention.

The following abbreviations and definitions are used: % (mass percent); % area (percent area, a/a %); eq. (molar equivalent relative to 1-(2-ethyl-butyl)-cyclohexanecarbonitrile); g (gram); GC FID (gas chromatography flame ionization detector); h (hour); HCl (hydrochloric acid); $H_2O$ (water); HPLC (High-Performance Liquid Chromatography); ISP (Isotopic Spin Population); KOH (Potassium Hydroxide); mL (milliliter); and NaOH (Sodium hydroxide);

EXAMPLE 1

Synthesis of 1-(2-Ethyl-butyl)-cyclohexanecarboxylic acid 1-(2-Ethyl-butyl)-cyclohexanecarbonitrile (9.67 g, 50 mmol, 1 eq), 8.8 g of aqueous NaOH (50% solution in water, 110 mmol, 2.2 eq), and methanol (16 g, 500 mmol, 10 eq) were charged at ambient temperature into a 50 mL Hastelloy C22 autoclave, which was sealed. The reaction mixture was vigorously stirred in the autoclave at 200° C. for 16 h. After cooling to ambient temperature, the pressure in the autoclave was released and the contents of the vessel were transferred into a mixture of $H_2O$ (20 mL), 31.4 g of HCl (25% solution, 215 mmol, 4.3 eq) and heptane (16 mL) in an Erlenmeyer flask.

A second batch was performed applying the same procedure as described above, using the same autoclave. The second reaction mass combined with the reaction mass from the first run, in the Erlenmeyer flask, and the pH of the aqueous phase was adjusted to between 1 and 2 by adding HCl (25%). The heterogeneous reaction mass was then separated at ambient temperature into two phases. The aqueous phase was backwashed with heptane (10 mL) and the extract combined with the organic phase from the first split. The combined organics were washed twice with $H_2O$ (2 mL) and evaporated in vacuo at under 50° C. After evaporation a pale yellow oil (20.7 g) was obtained.

A sample of the crude oil was derivatized with diazomethane and analyzed by GC-FID. Based on this analysis, the product oil contains: 0.11 g (0.57 mmol, 0.0057 eq, 0.5% area) unconverted 1-(2-ethyl-butyl)-cyclohexanecarbonitrile, 0.095 g (0.45 mmol, 0.0045 eq, 0.5% area) 1-(2-ethylbutyl)-cyclohexanecarboxylic acid amide, and 19.98 g (94.1 mmol, 0.94 eq, 98.2% area) 1-(2-ethyl-butyl)-cyclohexanecarboxylic acid. The yield of 1-(2-ethyl-butyl)-cyclohexanecarboxylic acid is 94.1% mole.

EXAMPLE 2

Synthesis of
1-(2-Ethyl-butyl)-cyclohexanecarboxylic acid 1-(2-Ethyl-butyl)-cyclohexanecarbonitrile (9.67 g, 50 mmol, 1 eq), solid NaOH (98%, 4.48 g, 110 mmol, 2.2 eq), $H_2O$ (2.61 g, 145 mmol, 2.9 eq), and methanol (16 g, 500 mmol, 10 eq) were charged at ambient temperature into a 50 mL Hastelloy C22 autoclave, which was sealed. The reaction mixture was vigorously stirred in the autoclave at 200° C. for 16 h. After cooling to ambient temperature, the pressure in the autoclave was released and the contents of the vessel were transferred into a mixture of $H_2O$ (20 ml), 34 g of HCl (25%, 233 mmol, 4.7 eq), and heptane (30 ml) in an Erlenmeyer flask.

A second batch was performed applying the same procedure as described above, using the same autoclave. The second reaction mass combined with the reaction mass from the first run in the Erlenmeyer flask, and the pH of the aqueous phase was adjusted to 0.6 by adding 30.8 g of HCl (25%, 211 mmol, 4.2 eq). The heterogeneous reaction mass was then separated at ambient temperature into two phases. The aqueous phase was backwashed twice with heptane (20 ml) and the extract combined with the organic phase from the first split. The combined organics were washed twice with $H_2O$ (5 ml) and evaporated in vacuo at 60° C. After evaporation, a pale yellow oil (20.65 g) was obtained.

A sample of the crude oil was derivatized with diazomethane and analyzed by GC-FID. Based on this analysis, the product oil contains: 0.2 g (1.06 mmol, 0.0106 eq, 1.0% area) unconverted 1-(2-ethyl-butyl)-cyclohexanecarbonitrile, 0.13 g (0.6 mmol, 0.006 eq, 0.6% area) of 1-(2-ethyl-butyl)-cyclohexanecarboxylic acid amide, and 19.7 g (93.0 mmol, 0.93 eq, 97.4% area) 1-(2-ethyl-butyl)-cyclohexanecarboxylic acid. The yield of 1-(2-ethyl-butyl)-cyclohexanecarboxylic acid is 92.9% mole.

EXAMPLE 3

Synthesis of
1-(2-Ethyl-butyl)-cyclohexanecarboxylic acid 1-(2-Ethyl-butyl)-cyclohexanecarbonitrile (6.07 g, 31.4 mmol, 1 eq), 5.53 g of aqueous NaOH (50% solution in water, 69 mmol, 2.2 eq), and methanol (10.1 g, 315 mmol, 10 eq) were charged at ambient temperature into a 50 mL Hastelloy C22 autoclave, which was sealed. The reaction mixture was vigorously stirred in the autoclave at 200° C. for 16 h. After cooling to ambient temperature, the pressure in the autoclave was released and the contents of the vessel were transferred into a mixture of $H_2O$ (12 ml), 12 g of HCl (25%), and heptane (10 ml). Afterwards, the pH of the aqueous phase in the autoclave was adjusted to 1.5 by adding 2.1 g of HCl (25%). Total addition of HCl was 14.1 g (25%, 97 mmol, 3.1 eq).

From the heterogeneous reaction mass a first sample from the upper organic layer was taken and analyzed by GC-FID. Based on this analysis, the organic layer contains 98.4% area of 1-(2-ethyl-butyl)-cyclohexanecarboxylic acid, 0.7% area unconverted 1-(2-ethyl-butyl)-cyclohexanecarbonitrile, 0.7% area of the intermediate 1-(2-ethyl-butyl)-cyclohexanecarboxylic acid amide.

A second sample from the organic phase was evaporated under 55° C./20 mbar, derivatized with diazomethane and analyzed by GC-FID: 98.5% area 1-(2-ethyl-butyl)-cyclohexanecarboxylic acid, 0.4% area unconverted 1-(2-ethylbutyl)-cyclohexanecarbonitrile, 0.6% area of the intermediate 1-(2-ethyl-butyl)-cyclohexanecarboxylic acid amide.

EXAMPLE 4

Synthesis of
1-(2-Ethyl-butyl)-cyclohexanecarboxylic acid 1-(2-Ethyl-butyl)-cyclohexanecarbonitrile (6.07 g, 31.4 mmol, 1 eq), 9.2 g of aqueous NaOH (30% solution in water, 69 mmol, 2.2 eq), and methanol (10.1 g, 315 mmol 10 eq) were charged at ambient temperature into a 50 mL Hastelloy C22 autoclave, which was sealed. The reaction mixture was vigorously stirred in the autoclave at 200° C. for 16 h. After cooling to ambient temperature, the pressure in the autoclave was released and the contents of the vessel were transferred into a mixture of $H_2O$ (12 ml), HCl (25%, 12 g), and heptane (10 ml). Afterwards, the pH of the aqueous phase in the reactor was set between 1 and 2 by adding 2.1 g of HCl (25%). Total addition of HCl was 14.1 g (25%, 97 mmol, 3.1 eq).

From the heterogeneous reaction mass, a first sample from the upper organic layer was taken and analyzed by GC-FID. Based on this analysis, the organic layer contains 97.2% area 1-(2-ethyl-butyl)-cyclohexanecarboxylic acid, 0.9% area unconverted 1-(2-ethyl-butyl)-cyclohexanecarbonitrile, 1.3% area of the intermediate 1-(2-ethyl-butyl)-cyclohexanecarboxylic acid amide.

A second sample from the organic phase was evaporated under 55° C./20 mbar, derivatized with diazomethane and analyzed by GC-FID: 97.4% area 1-(2-ethyl-butyl)-cyclohexanecarboxylic acid, 0.7% area unconverted 1-(2-ethylbutyl)-cyclohexanecarbonitrile, 1.1% area of the intermediate 1-(2-ethyl-butyl)-cyclohexanecarboxylic acid amide.

EXAMPLE 5

Synthesis of
1-(2-Ethyl-butyl)-cyclohexanecarboxylic acid 1-(2-Ethyl-butyl)-cyclohexanecarbonitrile (9.67 g, 50 mmol, 1 eq), 8.8 g of aqueous NaOH (50% solution in water, 110 mmol, 2.2 eq), and ethanol (16.1 g, 350 mmol, 7 eq) were charged at ambient temperature into a 50 mL Hastelloy C22 autoclave, which was sealed. The reaction mixture was vigorously stirred in the autoclave at 200° C. for 20 h. After cooling to ambient temperature, the pressure in the autoclave was released and the contents of the vessel were transferred into a mixture of $H_2O$ (20 ml), 25.2 g of HCl (25%, 173 mmol, 3.5 eq), and heptane (16 ml).

A second batch was performed applying the same procedure as described above, using the same autoclave. The second reaction mass, combined with the reaction mass from the first run, in the Erlenmeyer flask, and the pH of the aqueous phase was adjusted to 1.5 by adding 21.4 g of HCl (25%, 147 mmol, 2.9 eq). The heterogeneous reaction mass was then separated at ambient temperature into two phases. The aqueous phase was backwashed with heptane (10 ml) and the extract combined with the organic phase from the first split. The combined organics were washed with $H_2O$ (2 ml) and evaporated in vacuo at 55° C. After evaporation a pale yellow oil (21.09 g) was obtained.

A sample of the crude oil was derivatized with diazomethane and analyzed by GC-FID. Based on this analysis, the organic layer contains: 0.24 g (1.23 mmol, 0.012 eq, 1.2% area) unconverted 1-(2-ethyl-butyl)-cyclohexanecarbonitrile, 0.4 g (1.89 mmol, 0.019 eq, 2.0% area) 1-(2-ethyl-butyl)-cyclohexanecarboxylic acid amide, and 19.5 g (91.8 mmol, 0.92 eq, 95.9% area) 1-(2-ethyl-butyl)-cyclohexanecarboxylic acid. The yield of 1-(2-ethyl-butyl)-cyclohexanecarboxylic acid is 91.8% mole.

EXAMPLE 6

Synthesis of 1-(2-Ethyl-butyl)-cyclohexanecarboxylic acid 1-(2-Ethyl-butyl)-cyclohexanecarbonitrile (9.67 g, 50 mmol, 1 eq), 8.8 g of aqueous NaOH (50% solution in water, 110 mmol, 2.2 eq), and benzyl alcohol (20.5 g, 190 mmol 3.8 eq) were charged at ambient temperature into a 50 mL Hastelloy C22 autoclave, which was sealed. The reaction mixture was vigorously stirred in the autoclave at 200° C. for 16 h. After cooling to ambient temperature, the pressure in the autoclave was released and the contents of the vessel were transferred into a mixture of $H_2O$ (20 ml), and heptane (24 ml).

The organic phase was removed and the aqueous phase was adjusted to a pH of 2 by adding 20.1 g HCl (25%, 140 mmol, 2.75 eq). The product was extracted from the aqueous phase with heptane (24 ml) at ambient temperature. The organic phase was analyzed by GC-FID. Based on this analysis, the organic layer contains 90.1% area 1-(2-ethyl-butyl)-cyclohexanecarboxylic acid, 3.9% area unconverted 1-(2-ethyl-butyl)-cyclohexanecarbonitrile, and 3.9% area of the intermediate 1-(2-ethyl-butyl)-cyclohexanecarboxylic acid amide.

EXAMPLE 7

Synthesis of 1-(2-Ethyl-butyl)-cyclohexanecarboxylic acid 1-(2-Ethyl-butyl)-cyclohexanecarbonitrile (6.07 g, 31.4 mmol, 1 eq), 5.53 g of aqueous NaOH (50% solution in water, 69 mmol, 2.2 eq), and methanol (10.1 g, 315 mmol 10 eq) were charged at ambient temperature into a 50 mL Hastelloy C22 autoclave, which was sealed. The autoclave was equipped with an agitator, and electrical heating on the jacket. The reaction mixture was vigorously stirred in the autoclave at 180° C. for 26 h. After cooling to ambient temperature, the pressure in the autoclave was released and the contents of the vessel were transferred into a mixture of $H_2O$ (12 ml), 12 g of HCl (25%), and heptane (10 ml).

Afterwards the pH of the aqueous phase in the autoclave was adjusted to 2 by adding 2.3 g of HCl (25%). Total addition of HCl was 14.3 g (25%, 98 mmol, 3.1 eq).

From the heterogeneous reaction mass a first sample from the upper organic layer was taken and analyzed by GC-FID. Based on this analysis, the organic layer contains 95.2% area 1-(2-ethyl-butyl)-cyclohexanecarboxylic acid, 0.9% area unconverted 1-(2-ethyl-butyl)-cyclohexanecarbonitrile, 3.6% area of the intermediate 1-(2-ethyl-butyl)-cyclohexanecarboxylic acid amide.

EXAMPLE 8

Synthesis of 1-(2-Ethyl-butyl)-cyclohexanecarboxylic acid 1-(2-Ethyl-butyl)-cyclohexanecarbonitrile (6.07 g, 31.4 mmol, 1 eq), 2.82 g of solid NaOH (98%, 69 mmol, 2.2 eq), $H_2O$ (1.64 g, 91 mmol, 2.9 eq), and methanol (10.1 g, 315 mmol 10 eq) were charged at ambient temperature into a 50 mL Hastelloy C22 autoclave, which was sealed. The reaction mixture was vigorously stirred in the autoclave at 230° C. for 7 h. After cooling to ambient temperature, the pressure in the autoclave was released and the contents of the vessel were transferred into a mixture of $H_2O$ (6 ml), 20 g of HCl (25%), and heptane (10 ml). Afterwards the pH of the aqueous phase in the autoclave was adjusted to 2 by adding 2 g of HCl (25%). Total addition of HCl was 22 g (25%, 150 mmol, 4.8 eq).

From the heterogeneous reaction mass a sample from the upper organic layer was taken and analyzed by GC-FID. Based on this analysis, the organic layer contains 97.5% area 1-(2-ethyl-butyl)-cyclohexanecarboxylic acid, 2.0% area unconverted 1-(2-ethyl-butyl)-cyclohexanecarbonitrile, 0.4% area of the intermediate 1-(2-ethyl-butyl)-cyclohexanecarboxylic acid amide.

EXAMPLE 9

Synthesis of 1-(2-Ethyl-butyl)-cyclohexanecarboxylic acid 1-(2-Ethyl-butyl)-cyclohexanecarbonitrile (6.07 g, 31.4 mmol, 1 eq), 3.45 g of solid NaOH (98%, 85 mmol, 2.7 eq), $H_2O$ (1.12 g, 62 mmol, 2 eq), and methanol (10.1 g, 315 mmol, 10 eq) were charged at ambient temperature into a 50 mL Hastelloy C22 autoclave, which was sealed. The reaction mixture was vigorously stirred in the autoclave at 200° C. for 7 h. After cooling to ambient temperature, the pressure in the autoclave was released and the contents of the vessel were transferred into a mixture of $H_2O$ (6 ml), 19 g of HCl (25%), and heptane (10 ml). Afterwards the pH of the aqueous phase in the autoclave was adjusted to 2 by adding 2 g of HCl (25%). Total addition of HCl was 21 g (25%, 145 mmol, 4.6 eq).

From the heterogeneous reaction mass a sample from the upper organic layer was taken and analyzed by GC-FID. Based on this analysis, the organic layer contains 92.1% area 1-(2-ethyl-butyl)-cyclohexanecarboxylic acid, 5.4% area unconverted 1-(2-ethyl-butyl)-cyclohexanecarbonitrile, 2.5% area of the intermediate 1-(2-ethyl-butyl)-cyclohexanecarboxylic acid amide.

EXAMPLE 10

Synthesis of 1-(2-Ethyl-butyl)-cyclohexanecarboxylic acid 1-(2-Ethyl-butyl)-cyclohexanecarbonitrile (6.07 g, 31.4 mmol, 1 eq), 1.92 g of solid NaOH (98%, 47 mmol, 1.5 eq), $H_2O$ (1.66 g, 92 mmol, 2.9 eq), and methanol (10.1 g, 315 mmol 10 eq) were charged at ambient temperature into a 50 mL Hastelloy C22 autoclave, which was sealed. The reaction mixture was vigorously stirred in the autoclave at 200° C. for 7 h. After cooling to ambient temperature, the pressure in the autoclave was released and the contents of the vessel were transferred into a mixture of $H_2O$ (6 ml), 13 g of HCl (25%), and heptane (10 ml). Afterwards the pH of the aqueous phase in the autoclave was adjusted to 2 by adding 2 g of HCl (25%). Total addition of HCl was 15 g (25%, 100 mmol, 3.3 eq).

From the heterogeneous reaction mass, a sample from the upper organic layer was taken and analyzed by GC-FID. Based on this analysis, the organic layer contains 83.3% area 1-(2-ethyl-butyl)-cyclohexanecarboxylic acid, 7.7% area unconverted 1-(2-ethyl-butyl)-cyclohexanecarbonitrile, 8.9% area of the intermediate 1-(2-ethyl-butyl)-cyclohexanecarboxylic acid amide.

EXAMPLE 11

Synthesis of 1-(2-Ethyl-butyl)-cyclohexanecarboxylic acid 1-(2-Ethyl-butyl)-cyclohexanecarbonitrile (6.07 g, 31.4 mmol, 1 eq), 3.84 g of solid NaOH (98%, 94 mmol, 3 eq), H$_2$O (1.62 g, 90 mmol, 2.9 eq), and methanol (10.1 g, 315 mmol, 10 eq) were charged at ambient temperature into a 50 mL Hastelloy C22 autoclave, which was sealed. The reaction mixture was vigorously stirred in the autoclave at 200° C. for 7 h. After cooling to ambient temperature, the pressure in the autoclave was released and the contents of the vessel were transferred into a mixture of H$_2$O (12 ml), 19 g of HCl (25%), and heptane (10 ml). Afterwards the pH of the aqueous phase in the autoclave was adjusted to 2 by adding 2 g of HCl (25%). Total addition of HCl was 21 g (25%, 145 mmol, 4.6 eq).

From the heterogeneous reaction mass a sample from the upper organic layer was taken and analyzed by GC-FID. Based on this analysis, the organic layer contains 90.6% area 1-(2-ethyl-butyl)-cyclohexanecarboxylic acid, 6.6% area unconverted 1-(2-ethyl-butyl)-cyclohexanecarbonitrile, 2.7% area of the intermediate 1-(2-ethyl-butyl)-cyclohexanecarboxylic acid amide.

EXAMPLE 12

Synthesis of 1-(2-Ethyl-butyl)-cyclohexanecarboxylic acid 1-(2-Ethyl-butyl)-cyclohexanecarbonitrile (6.07 g, 31.4 mmol, 1 eq), 2.82 g of solid NaOH (98%, 69 mmol, 2.2 eq), H$_2$O (1.64 g, 91 mmol, 2.9 eq), and methanol (10.1 g, 315 mmol 10 eq) were charged at ambient temperature into a 50 mL Hastelloy C22 autoclave, which was sealed. The reaction mixture was vigorously stirred in the autoclave at 200° C. for 7 h. After cooling to ambient temperature, the pressure in the autoclave was released and the contents of the vessel were transferred into a mixture of H$_2$O (6 ml), 18 g of HCl (25%), and heptane (10 ml) Afterwards, the pH of the aqueous phase in the autoclave was adjusted to 2 by adding 2 g of HCl (25%). Total addition of HCl was 20 g (25%, 137 mmol, 4.4 eq).

From the heterogeneous reaction mass (two liquid phases) a sample from the upper organic layer was taken and analyzed by GC-FID. Based on this analysis, the organic layer contains 90.2% area 1-(2-ethyl-butyl)-cyclohexanecarboxylic acid, 5.3% area unconverted 1-(2-ethyl-butyl)-cyclohexanecarbonitrile, 4.5% area of the intermediate 1-(2-ethyl-butyl)-cyclohexanecarboxylic acid amide.

EXAMPLE 13

Synthesis of 1-(2-Ethyl-butyl)-cyclohexanecarboxylic acid 1-(2-Ethyl-butyl)-cyclohexanecarbonitrile (8.31 g, 43 mmol, 1 eq), 3.86 g of solid NaOH (98%, 95 mmol, 2.2 eq), H$_2$O (2.25 g, 125 mmol, 2.9 eq), and methanol (6.9 g, 215 mmol, 5 eq) were charged at ambient temperature into a 50 mL Hastelloy C22 autoclave, which was sealed. The reaction mixture was vigorously stirred in the autoclave at 200° C. for 7 h. After cooling to ambient temperature, the pressure in the autoclave was released and the contents of the vessel were transferred into a mixture of H$_2$O (12 ml), 26 g of HCl (25%), and heptane (10 ml). Afterwards the pH of the aqueous phase in the autoclave was adjusted to 2 by adding 2.6 g of HCl (25%). Total addition of HCl was 28.6 g (25%, 196 mmol, 4.6 eq).

From the heterogeneous reaction mass a sample from the upper organic layer was taken and analyzed by GC-FID. Based on this analysis, the organic layer contains 79.7% area 1-(2-ethyl-butyl)-cyclohexanecarboxylic acid, 9.6% area unconverted 1-(2-ethyl-butyl)-cyclohexanecarbonitrile, 10.4% area of the intermediate 1-(2-ethyl-butyl)-cyclohexanecarboxylic acid amide.

EXAMPLE 14

Synthesis of 1-(2-Ethyl-butyl)-cyclohexanecarboxylic acid 1-(2-Ethyl-butyl)-cyclohexanecarbonitrile (7.03 g, 36.4 mmol, 1 eq), 3.26 g of solid NaOH (98%, 80 mmol, 2.2 eq), H$_2$O (1.9 g, 106 mmol, 2.9 eq), and methanol (8.7 g, 272 mmol 7.5 eq) were charged at ambient temperature into a 50 mL Hastelloy C22 autoclave, which was sealed. The reaction mixture was vigorously stirred in the autoclave at 200° C. for 7 h. After cooling to ambient temperature, the pressure in the autoclave was released and the contents of the vessel were transferred into a mixture of H$_2$O (12 ml), 19 g of HCl (25%), and heptane (10 ml) Afterwards the pH of the aqueous phase in the autoclave was adjusted to 2 by adding 2.9 g of HCl (25%). Total addition of HCl was 21.9 g (25%, 150 mmol, 4.1 eq).

From the heterogeneous reaction mass a sample from the upper organic layer was taken and analyzed by GC-FID. Based on this analysis, the organic layer contains 91.1% area 1-(2-ethyl-butyl)-cyclohexanecarboxylic acid, 5.4% area unconverted 1-(2-ethyl-butyl)-cyclohexanecarbonitrile, 3.2% area of the intermediate 1-(2-ethyl-butyl)-cyclohexanecarboxylic acid amide.

EXAMPLE 15

Synthesis of 1-(2-Ethyl-butyl)-cyclohexanecarboxylic acid 1-(2-Ethyl-butyl)-cyclohexanecarbonitrile (6.07 g, 31.4 mmol, 1 eq), 5.51 g of solid potassium hydroxide (86%, 85 mmol, 2.7 eq), H$_2$O (0.42 g, 23 mmol, 0.7 eq), and methanol (10.1 g, 315 mmol, 10 eq) were charged at ambient temperature into a 50 mL Hastelloy C22 autoclave, which was sealed. The reaction mixture was vigorously stirred in the autoclave at 200° C. for 7 h. After cooling to ambient temperature, the pressure in the autoclave was released and the contents of the vessel were transferred into a mixture of H$_2$O (12 ml), 12 g of HCl (25%), and heptane (20 ml). Afterwards the pH of the aqueous phase in the autoclave was adjusted to 2 by adding 2 g of HCl (25%). Total addition of HCl was 14 g (25%, 96 mmol, 3.1 eq).

From the heterogeneous reaction mass a sample from the upper organic layer was taken and analyzed by GC-FID. Based on this analysis, the organic layer contains 67.2% area 1-(2-ethyl-butyl)-cyclohexanecarboxylic acid, 17.7% area unconverted 1-(2-ethyl-butyl)-cyclohexanecarbonitrile, 15.0% area of the intermediate 1-(2-ethyl-butyl)-cyclohexanecarboxylic acid amide.

EXAMPLE 16

Synthesis of 1-(2-Ethyl-butyl)-cyclohexanecarboxylic acid 1-(2-Ethyl-butyl)-cyclohexanecarbonitrile (6.07 g, 31.4 mmol, 1 eq), 5.51 g of solid KOH (86%, 85 mmol, 2.7 eq), H₂O (0.42 g, 23 mmol, 0.7 eq), and 1-propanol (10.2 g, 170 mmol 5.4 eq) were charged at ambient temperature into a 50 mL Hastelloy C22 autoclave, which was sealed. The reaction mixture was vigorously stirred in the autoclave at 200° C. for 7 h. After cooling to ambient temperature, the pressure in the autoclave was released and the contents of the vessel were transferred into a mixture of H₂O (12 ml), 11 g of HCl (25%), and heptane (20 ml). Afterwards the pH of the aqueous phase in the autoclave was adjusted to 2 by adding 2 g of HCl (25%). Total addition of HCl was 13 g (25%, 89 mmol, 2.8 eq).

From the heterogeneous reaction mass a sample from the upper organic layer was taken and analyzed by GC-FID. Based on this analysis, the organic layer contains 47.9% area 1-(2-ethyl-butyl)-cyclohexanecarboxylic acid, 15.4% area unconverted 1-(2-ethyl-butyl)-cyclohexanecarbonitrile, 36.2% area of the intermediate 1-(2-ethyl-butyl)-cyclohexanecarboxylic acid amide.

EXAMPLE 17

Synthesis of 1-(2-Ethyl-butyl)-cyclohexanecarboxylic acid 1-(2-Ethyl-butyl)-cyclohexanecarbonitrile (6.07 g, 31.4 mmol, 1 eq), 5.51 g of solid KOH (86%, 85 mmol, 2.7 eq), H₂O (0.42 g, 23 mmol, 0.7 eq), and 2-amino ethanol (12.5 g, 204 mmol 6.5 eq) were charged at ambient temperature into a 50 mL Hastelloy C22 autoclave, which was sealed. The reaction mixture was vigorously stirred in the autoclave at 200° C. for 7 h. After cooling to ambient temperature, the pressure in the autoclave was released and the contents of the vessel were transferred into a mixture of H₂O (12 ml), 39 g of HCl (25%), and heptane (10 ml). Afterwards the pH of the aqueous phase in the autoclave was adjusted to 2 by adding 2 g of HCl (25%). Total addition of HCl was 41 g (25%, 281 mmol, 8.9 eq).

From the heterogeneous reaction mass, a sample from the upper organic layer was taken and analyzed by GC-FID. Based on this analysis, the organic layer contains 70.2% area 1-(2-ethyl-butyl)-cyclohexanecarboxylic acid, 21.2% area unconverted 1-(2-ethyl-butyl)-cyclohexanecarbonitrile, 7.4% area of the intermediate 1-(2-ethyl-butyl)-cyclohexanecarboxylic acid amide.

EXAMPLE 18

Synthesis of 1-(2-Ethyl-butyl)-cyclohexanecarboxylic acid 1-(2-Ethyl-butyl)-cyclohexanecarbonitrile (191.4 g, 990 mmol, 1 eq), solid NaOH (98%, 87.5 g, 2.19 mol, 2.2 eq), H₂O (87.5 g, 4.85 mol, 4.9 eq), and methanol (319 g, 9.96 mol, 10.1 eq) were charged at ambient temperature into a 1.8 L Hastelloy C22 autoclave, which was sealed. The reaction mixture was heated under vigorous stirring to 204° C. The reaction mass was kept at 204° C. for 30 minutes and the pressure was allowed to increase up to 30 bar. When the pressure had reached 30 bar, the pressure was controlled at 30 bar by releasing ammonia/methanol vapor via a small needle valve. The needle valve was closed after about 5 hours age time at 204° C. After a further 10 h age time at 204° C. (30.6 barg) the reaction mass was cooled down to 70° C. and unloaded (627 g).

From the unloaded reaction mass, an aliquot (40.0 g) was mixed with H₂O (24.0 g), 27.9 g of HCl (25%), and heptane (20 ml). The pH of the aqueous phase was 1.5. From the heterogeneous reaction mass a sample from the upper organic layer was taken and analyzed by GC-FID. Based on this analysis, the organic layer contains 0.3% area of unconverted 1-(2-ethyl-butyl)-cyclohexanecarbonitrile, 0.9% area of 1-(2-ethyl-butyl)-cyclohexanecarboxylic acid amide, and 98.4% area of 1-(2-ethyl-butyl)-cyclohexanecarboxylic acid.

EXAMPLE 19

Synthesis of 1-(2-Ethyl-butyl)-cyclohexanecarboxylic acid 1-(2-Ethyl-butyl)-cyclohexanecarbonitrile (191.4 g, 990 mmol, 1 eq), and 174.9 g of aqueous NaOH (50% solution in H₂O, 2186 mmol, 2.2 eq), were charged at ambient temperature into a 1 L autoclave, which was sealed. All parts of the autoclave that were in direct contact with the reaction mass were made of nickel (in-liner, agitator, temperature sensor). The reaction mixture was vigorously stirred in the autoclave at 250° C. for 22 h. After cooling to ambient temperature, the pressure in the autoclave was released. The reaction mass was then reheated to 60° C., and dissolved by the addition of heptane (300 ml) and 320 g aqueous HCl (25%). The heterogeneous reaction mass was then separated at ambient temperature into two phases. The organic layer was azoetropically dried using a decanter (ambient pressure, 130° C. jacket temperature). After drying, 361.4 g of a pale yellow product solution was obtained. A sample of this product solution was derivatized with diazomethane and analyzed by GC-FID. Based on this analysis, the product solution contains: 0.1 g (0.5 mmol, 0.05% area) unconverted 1-(2-ethyl-butyl)-cyclohexanecarbonitrile, 0.1 g (0.4 mmol, 0.04% area) 1-(2-ethyl-butyl)-cyclohexanecarboxylic acid amide, and 189 g (891 mmol, 99.1% area) 1-(2-ethyl-butyl)-cyclohexanecarboxylic acid. The yield of 1-(2-ethyl-butyl)-cyclohexanecarboxylic acid is 90% mole.

EXAMPLE 20

Synthesis of 1-(2-Ethyl-butyl)-cyclohexanecarboxylic acid 1-(2-Ethyl-butyl)-cyclohexanecarbonitrile (152.0 g, 786 mmol, 1 eq), 69.1 g of NaOH (98%, 1693 mmol, 2.2 eq), and H₂O (267.4 g, 14.9 mol, 18.9 eq), were charged at ambient temperature into a 1 L autoclave, which was sealed. All parts of the autoclave that were in direct contact with the reaction mass were made of nickel (in-liner, agitator, temperature sensor). The reaction mixture was vigorously stirred in the autoclave at 250° C. for 17 h. After cooling to ambient temperature, the pressure in the autoclave was released and heptane (200 g) was added to the reaction mass. Afterwards, the pH of the reaction mass was set below 2 by the addition of 324 g aqueous HCl (25%). The heterogeneous reaction mass was then separated at ambient temperature into two phases. The organic layer was azoetropically dried using a decanter (ambient pressure, 130° C. jacket temperature). After drying, 338.4 g of a pale yellow product solution was obtained. A sample of this product solution was derivatized with diazomethane and analyzed by GC-FID. Based on this analysis, the product solution contains: 0.4 g (2.3 mmol, 0.3% area) unconverted 1-(2-ethyl-butyl)-cyclohexanecarbonitrile, 0.4 g (1.7 mmol, 0.2% area) 1-(2-ethyl-butyl)-cyclohexanecarboxylic acid amide, and 158 g (743 mmol, 98.7% area) 1-(2- ethyl-butyl)-cyclohexanecarboxylic acid. The yield of 1-(2-ethyl-butyl)-cyclohexanecarboxylic acid is 94.5% mole.

EXAMPLE 21

Synthesis of
1-(2-Ethyl-butyl)-cyclohexanecarboxylic acid 1-(2-Ethyl-butyl)-cyclohexanecarbonitrile (191.4 g, 990 mmol, 1 eq), 87.5 g of NaOH (98%, 2143 mmol, 2.2 eq), $H_2O$ (87.5 g, 4.9 mol, 4.9 eq), and 1-(2-ethyl-butyl)-cyclohexanecarboxylic acid (21.5 g, 99 mmol, 0.1 eq) were charged at ambient temperature into a 1 L autoclave, which was sealed. All parts of the autoclave that were in direct contact with the reaction mass were made of nickel (in-liner, agitator, temperature sensor). The reaction mixture was vigorously stirred in the autoclave at 250° C. for 16 h. After cooling to 40° C., the pressure in the autoclave was released. The reaction mass was then reheated to 60° C., and dissolved by the addition of heptane (340 ml), 315.3 g aqueous HCl (25%), and 40 g $H_2O$. The heterogeneous reaction mass was then separated at ambient temperature into two phases. The organic layer was azoetropically dried using a decanter (ambient pressure, 130° C. jacket temperature). After drying, 410.2 g of a pale yellow product solution was obtained. A sample of this product solution was derivatized with diazomethane and analyzed by GC-FID. Based on this analysis, the product solution contains: 0.5 g (2.4 mmol, 0.2% area) unconverted 1-(2-ethyl-butyl)-cyclohexanecarbonitrile, 0.2 g (1.0 mmol, 0.1% area) 1-(2-ethyl-butyl)-cyclohexanecarboxylic acid amide, and 219 g (1029 mmol, 98.5% area) 1-(2-ethyl-butyl)-cyclohexanecarboxylic acid. The yield of 1-(2-ethyl-butyl)-cyclohexanecarboxylic acid is 93.9% mole.

EXAMPLE 22

Synthesis of
1-(2-Ethyl-butyl)-cyclohexanecarboxylic acid 1-(2-Ethyl-butyl)-cyclohexanecarbonitrile (135.0 g, 698 mmol, 1 eq), 68.1 g of NaOH (98%, 1668 mmol, 2.4 eq), $H_2O$ (264 g, 14.7 mol, 21 eq), and 1-(2-ethyl-butyl)-cyclohexanecarboxylic acid (15.0 g, 71 mmol, 0.1 eq) were charged at ambient temperature into a 1 L autoclave, which was sealed. All parts of the autoclave that were in direct contact with the reaction mass were made of nickel (in-liner, agitator, temperature sensor). The reaction mixture was vigorously stirred in the autoclave at 250° C. for 17 h. After cooling to ambient temperature, the pressure in the autoclave was released and heptane (200 g) was added to the reaction mass. Afterwards the pH of the reaction mass was set below 2 by the addition of 323 g aqueous HCl (25%). The heterogeneous reaction mass was then separated at ambient temperature into two phases. The organic layer was azoetropically dried using a decanter (ambient pressure, 130° C. jacket temperature). After drying 365.5 g of a pale yellow product solution was obtained. A sample of this product solution was derivatized with diazomethane and analyzed by GC-FID. Based on this analysis, the product solution contains: 0.9 g (4.7 mmol, 0.6% area) unconverted 1-(2-ethyl-butyl)-cyclohexanecarbonitrile, 0.2 g (1.1 mmol, 0.2% area) 1-(2-ethyl-butyl)-cyclohexanecarboxylic acid amide, and 157 g (738 mmol, 97.7% area) 1-(2-ethyl-butyl) -cyclohexanecarboxylic acid. The yield of 1-(2-ethyl-butyl)-cyclohexanecarboxylic acid is 95.8% mole.

EXAMPLE 23

Flow Synthesis of
1-(2-Ethyl-butyl)-cyclohexanecarboxylic acid

A stream of 1-(2-ethyl-butyl)-cyclohexanecarbonitrile (0.5 g, 2.59 mmol) in tert-butanol (12.5 mL, 0.2 M, flow=0.18 mL/min; Knauer WellChrom HPLC K-501 pump) was combined with a second stream containing aqueous sodium hydroxide solution (2.0 M, 50 mL, flow=0.70 mL/min; Knauer WellChrom HPLC K-501 pump) using a custom made static micromixer (internal volume ca. 0.1 mL). The resulting mixture was directed through a stainless steel coil reactor (volume=53 mL, ID=2.1 mm; Supelco 304 stainless steel; nominal residence time of 1 h, which doesn't take the volume expansion of the solvent mixture into account) equipped with a total back pressure valve of 2500 psi and heated to 280° C. by means of a HP 6890 Series GC Oven System.

The tert-butanol was removed under reduced pressure and the aqueous layer extracted with heptane (50 mL). The organic phase was removed and the aqueous layer adjusted to a pH of 1 by addition of HCl (36%, 10 g). The product was extracted from the aqueous phase with heptane (3×50 mL) at ambient temperature. From the organic layer a sample was taken and analyzed by GC-FID. Based on this analysis, the organic layer contains 0.9% area of unconverted 1-(2-ethyl-butyl)-cyclohexanecarbonitrile, 0.4% area of 1-(2-ethyl-butyl)-cyclohexanecarboxylic acid amide, and 85% area of 1-(2-ethyl-butyl)-cyclohexanecarboxylic acid.

The combined organic layers were concentrated under reduced pressure and dried in vacuum to give an off-white solid of 1-(2-ethylethyl-butyl)-cyclohexanecarboxylic acid (0.43 g, 2.0 mol) in a 78% isolated yield.

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:
1. A process for the preparation of a compound of formula (I):

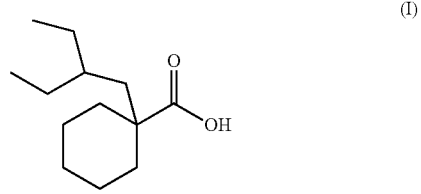

comprising reacting a compound of formula (II):

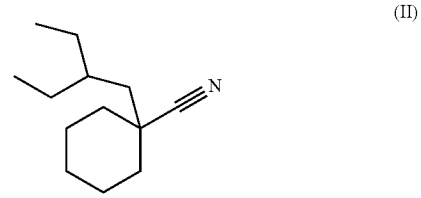

with a base wherein the base is an aqueous base, wherein the aqueous base is a solution comprising water and NaOH or an inorganic base, wherein the inorganic base is NaOH optionally in the presence of water, in the presence of methanol.

2. A process for the preparation of a compound of formula (I):

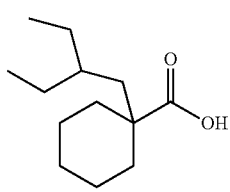

(I)

comprising reacting a compound of formula (II):

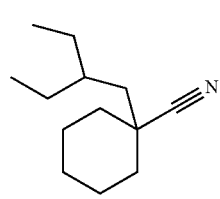

(II)

with aqueous NaOH, or with NaOH optionally in the presence of water, to obtain a compound of formula (III):

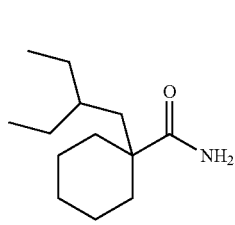

(III)

which is further hydrolysed to a compound of formula (IV):

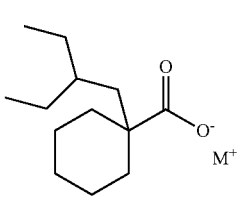

(IV)

wherein M⁺ is a Na⁺ counter ion, to obtain the compound of formula (I), in the presence of methanol.

3. A process for the preparation of a compound of formula (I):

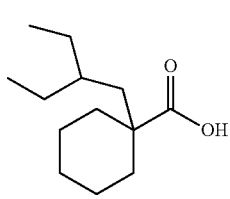

(I)

comprising reacting a compound of formula (II):

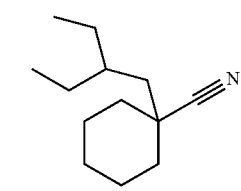

(II)

with aqueous NaOH to obtain a compound of formula (III):

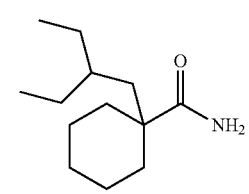

(III)

which is further hydrolysed to a compound of formula (IV):

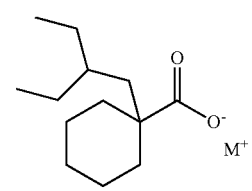

(IV)

wherein M⁺ is a Na⁺ counter ion, to obtain the compound of formula (I), in the presence of methanol.

4. The process according to claim 1, in the presence of at least one additional alcohol.

5. The process according claim 1, wherein at least 0.5 equivalents of the aqueous base with respect to compound of formula (I) is used.

6. The process according to claim 1, additionally comprising the step of reacting a halogenating agent in the presence of a tri-($C_1$-$C_5$)alkylamine with a compound of formula (I) as defined in claim 1, to obtain compound of formula (V), wherein X is I, Br, Cl or F:

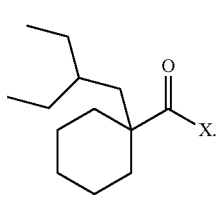

(V)

7. The process according to claim 6, further comprising the step of acylating a compound of the formula VI'

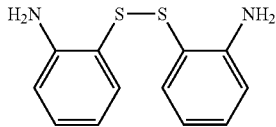
(VI')

with the compound of formula (V) to obtain a compound of formula VI:

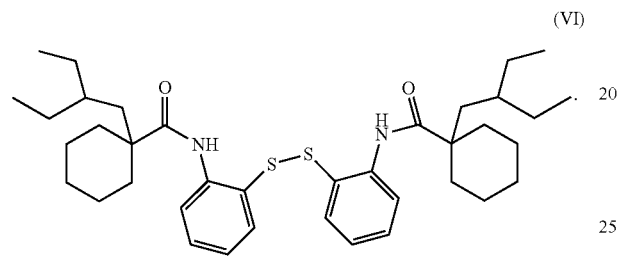
(VI)

8. The process according to claim 7, further comprising the step of reducing the compound of formula VI with a reducing agent to obtain a compound of formula VII :

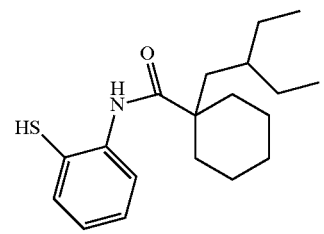
(VII)

9. The process according to claim 8, further comprising the step of acylating the compound of formula VII with $R^1C(O)X'$, wherein $R^1$ is a $(C_1-C_8)$alkyl and X' is I, Br, Cl or F, to obtain a compound of formula VIII:

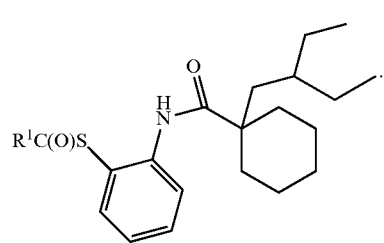
(VIII)

10. The process according to claim 1, wherein the process is semi-continuous or continuous.

* * * * *